United States Patent [19]
Mack et al.

[11] 4,136,825
[45] Jan. 30, 1979

[54] ORIFICE SEALING DEVICE

[75] Inventors: Frank J. Mack, Kinnelon; Michael P. Demkowicz, New Providence, both of N.J.

[73] Assignee: American Home Products Corporation, New York, N.Y.

[21] Appl. No.: 770,967

[22] Filed: Feb. 22, 1977

[51] Int. Cl.$^2$ .............................................. A61L 9/01
[52] U.S. Cl. ...................................... 239/44; 239/47; 239/50
[58] Field of Search ....................... 239/44, 47, 49, 50, 239/145; 222/187

[56] References Cited
U.S. PATENT DOCUMENTS

| | | | |
|---|---|---|---|
| 2,616,759 | 11/1952 | Walsh | 239/47 |
| 3,207,441 | 9/1965 | Schreiber | 239/44 X |

FOREIGN PATENT DOCUMENTS 688320  8/1930  France ........................................ 239/47

OTHER PUBLICATIONS

Baumeister & Marks, *Standard Handbook for Mechanical Engineers*, 7th Edition, McGraw-Hill, 1967, pp. (6-150)–(6-151).

*Primary Examiner*—Robert W. Saifer
*Attorney, Agent, or Firm*—Joseph Martin Weigman

[57] ABSTRACT

The disclosure is directed to a device for sealing the neck of apparatus which utilizes a wicking action to move liquid from the interior of a container to the surrounding atmosphere. The wick is disposed about an inner core of a cellulosic material which when wetted, expands to press the wick against the sides of the orifice. The wicking action is improved and the spilling of the contents through the orifice, in the event of an upset of the container, is prevented.

3 Claims, 6 Drawing Figures

ORIFICE SEALING DEVICE

This invention relates generally to apparatus which transfers a liquid from a container by a wicking action. More particularly, it relates to containers which are used for space air treatment in which a liquid treating composition is retained within a relatively narrow necked container, and is removed by a wick, one end of which extends into the liquid, the other end of which is connected to a support frame which may be disposed completely within the container and covered with a closure prior to use, and which upon removal of the closure, may be extended up into the surrounding air, thus bringing the liquid composition through the wick up into contact with the air to be treated.

One of the problems with such containers has been that they must be left open for extended periods in order to achieve their effectiveness. During the time they are open, they are susceptible to being accidentally overturned, resulting in a loss of the liquid contents.

It is an object of the present invention to provide a space air treating device which will not lose its liquid contents if overturned.

It is another object of the present invention to provide a space air treating device with an improved wicking action.

Other and further objects of the invention will be apparent from reading the following descrpition in conjunction with the drawings in which.

Figure 1:
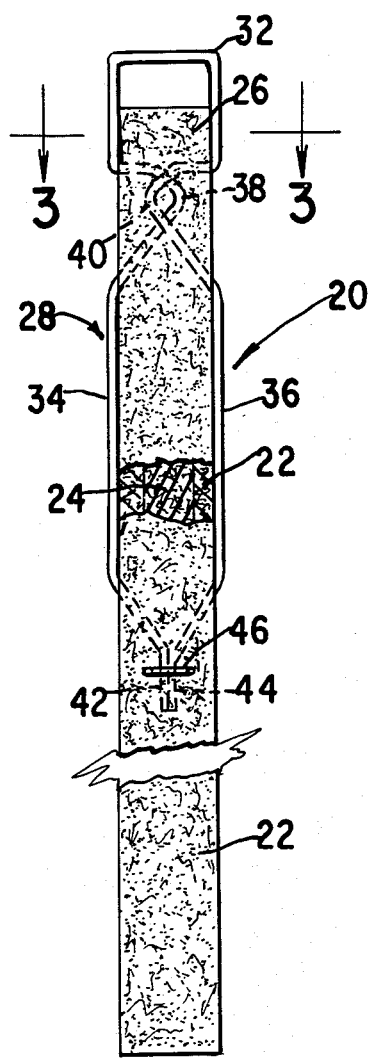
FIG. 1 is an elevational view, partly in section, of an improved wick and support frame, utilizing the features of the present invention.
Figure 2:
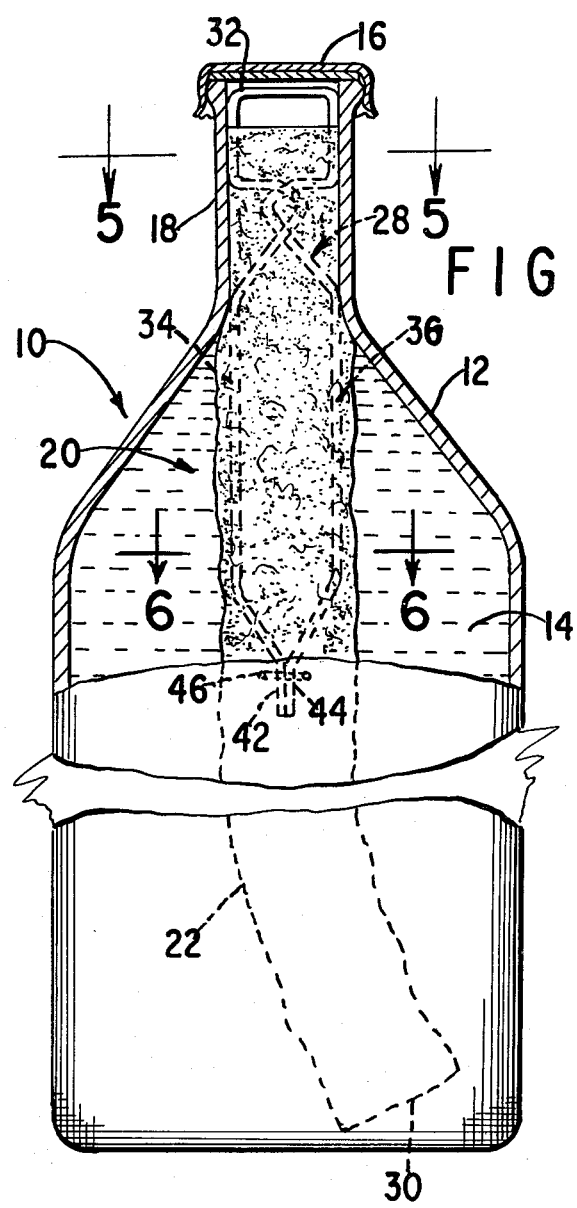
FIG. 2 is an elevational view, partly in section, of a space air treating device utilizing the improved wick of the present invention.

The objects of the present invention may be achieved with a space air treating device utilizing a liquid treating composition in which the liquid treating composition is removed from the container into contact with the air by a wick characterized by an inner core surrounded by the wick. The inner core is made up of a material which expands on contact with aqueous solutions and has an initial cross-sectional area, which when expanded, forces the wick against the container neck, thereby preventing the liquid treating composition from flowing from the container when the liquid level is higher than the container outlet, such as in an over-turned condition.

As may by seen in the drawings, the space air treating device 10 is made up of a container 12 holding a liquid treating composition 14 and sealed by a closure 16, and having a restricted neck portion 18, which is of a predetermined cross section smaller than the body of the container. The wick assembly 20 is made up of an elongated wick 22 which surrounds an inner core 24 and is fixedly connected near one end 26 to a support frame 28. The other end 30 extends into the liquid treating composition adjacent the bottom of the container. The support frame 28 is preferably made up of a stainless steel wire bent into a symmetrical spring configuration to define a pulling loop 32 at the upper end adjacent the outlet of the neck portion 18 and elongated side portions 34 and 36, connected to the loop by overlapping curved segments 38 and 40 which provides a springing action to facilitate sliding the wick assembly up and down in the neck 18. The side portions join together at their end portions 42 and 44. Preferably, the wick material 22 and inner core 24 are connected to the support frame by a staple 46 inserted over the end portions 42 and 44.

Figure 3:
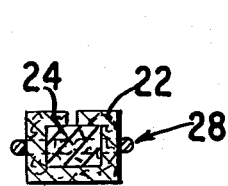
FIG. 3 is a sectional view taken generally along lines 3—3 of FIG. 1.
Figure 4:
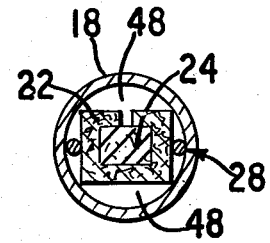
FIG. 4 is a horizontal sectional view showing the wick assembly in place in a container prior to wetting of the inner core.

As may be seen in FIG. 3, in the dry state the elongated wick 22 is placed around and nearly surrounds the inner core 24 and is connected to the support frame 28. In FIG. 4 is shown the dry wick assembly placed in the neck portion 18 and defining open areas 48.

Figure 5:
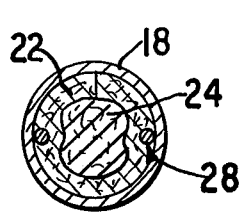
FIG. 5 is a cross sectional view taken generally lines 5—5 of FIG. 2 and showing the wick with the center core in an expanded condition.

FIG. 5 shows the status of the wick assembly after the inner core has become wetted. As may be seen, the inner core 24 has expanded and has pressed the elongated wick 22 against the neck portion 18 of the container eliminating the open areas.

Figure 6:
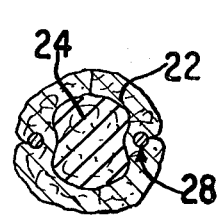
FIG. 6 is a cross sectional view taken generally lines 6—6 of FIG. 2 and showing a cross section of the wick out of the neck region.

In FIG. 6 is shown the nature of the expansion in the absence of a restaining means, such as a neck. As may be seen, the inner core is capable of greater expansion than is necessary to fill the neck 18.

In use, the closure 16 is removed, the loop 32 is engaged by the fingers and pulled upwardly so that only the bottom portion of the side portions 34 and 36 remain within the neck portion 18. If desired, the inner core may extend only through the same dimension length as the support frame 28. However, it is frequently more convenient to prepare a uniform wick that contains an inner core throughout its entire length.

The inner core may be any material which is capable of expanding when wetted by an aqueous solution to an amount sufficient to close the open areas 48 as shown in FIG. 4. Preferably, the inner core is a cellulosic material, a particular material has been Kimpak Type 201. The inner core preferably expands up to 75 percent in its wet condition over its dry condition, and preferably, is capable of absorbing up to 14–20 times, preferably 14 to 16 times its weight in water. The pressure force applied by the expansion should be at least two pounds and preferably forces of up to 3.4 pounds per thousand square feet.

It has been found that utilizing the cellulosic inner core increases the wicking action over the elongated wicks without a central core by about 4–6 percent.

The elongated wick is preferably pure non-woven cotton. The support frame preferably is made from steel wire. In a particularly advantageous embodiment, the support frame is constructed from type 430 ($R_B$82) stainless steel wire of 0.044 inches thickness having a tension strength of 140,000–180,000 psi. The staples also are preferably of steel and in a particularly advantageous embodiment, the staples are type 304 (annealed) stainless steel of 0.025 inch thickness having a tensile strength of 135,000–170,000 psi.

In one embodiment, the support frame is capable of expanding of 1⅛ inches across to firmly engage a neck which is about one inch internal diameter.

What is claimed is:

1. A space air treating device comprising in combination:

A. a container having a restricted neck;

B. a liquid air treating composition container in said container;
C. an elongated wick assembly disposed within said container in contact with said liquid composition and further comprising;
1. an outer member comprised of non-woven cotton;
2. an inner core comprised of cellulosic material, which when wetted by said liquid composition, absorbs from 14–20 times its weight of said liquid composition and expands from 100 to 175 percent of its original cross-sectional area, and which when wetted, expands against said restricted neck with a pressure of 2 to 3.4 pounds per thousand square feet, whereby said wick assembly fills the interior of said restricted wick and prevents said liquid composition from spilling from said container, while permitting said liquid composition to move by wicking action along said wick assembly into contact with the air to be treated.

2. A device as defined in claim 1 in which said inner core is present only within that portion of said wick which is in contact with said inner neck.

3. The space air treating device of claim 1 further comprising a frame connected to one end of said outer member, and being movably disposed within said restricted neck and being adapted to support said wick when withdrawn a predetermined distance from said neck.

* * * * *